US010893965B2

(12) United States Patent
Frohman

(10) Patent No.: US 10,893,965 B2
(45) Date of Patent: Jan. 19, 2021

(54) STENT DELIVERY CATHETER SYSTEM WITH SLOW SPEED CONTROL VIA PIN AND SLOT WITH FAST SPEED CONTROL TAB

(71) Applicant: Cardinal Health Switzerland 515 GmbH, Baar (CH)

(72) Inventor: Bruce Frohman, Saint Louis Park, MN (US)

( * ) Notice: Subject to any disclaimer, the term of this patent is extended or adjusted under 35 U.S.C. 154(b) by 185 days.

(21) Appl. No.: 16/169,793

(22) Filed: Oct. 24, 2018

(65) Prior Publication Data

US 2019/0125564 A1    May 2, 2019

Related U.S. Application Data

(60) Provisional application No. 62/578,494, filed on Oct. 29, 2017.

(51) Int. Cl.
*A61F 2/966* (2013.01)
*A61M 25/06* (2006.01)
*A61B 17/00* (2006.01)
*A61F 2/95* (2013.01)

(52) U.S. Cl.
CPC .......... *A61F 2/966* (2013.01); *A61M 25/0662* (2013.01); *A61B 2017/00407* (2013.01); *A61F 2/9517* (2020.05); *A61M 2025/0681* (2013.01)

(58) Field of Classification Search
CPC ........ A61F 2/9517; A61F 2/966; A61F 2/962; A61F 2002/9528; A61F 2002/9534; A61F 2/95–97; A61F 2/01; A61F 2/011; A61F 2/013; A61F 2002/9505–9623; A61B 2017/1205; A61B 2017/00407; A61B 17/12118; A61M 2025/0681; A61M 25/0662
See application file for complete search history.

(56) References Cited

U.S. PATENT DOCUMENTS

| 4,580,568 | A | 4/1986 | Gianturco |
| 4,732,152 | A | 3/1988 | Wallsten et al. |
| 6,019,778 | A | 2/2000 | Wilson et al. |
| 2011/0077621 | A1* | 3/2011 | Graham ............... A61M 25/01 604/528 |
| 2012/0290066 | A1* | 11/2012 | Nabulsi .................. A61F 2/966 623/1.11 |

FOREIGN PATENT DOCUMENTS

DE    102005051469 A1    4/2007

OTHER PUBLICATIONS

International Preliminary Report on Patentability in International Patent Application No. PCT/IB2018/001308, dated May 5, 2020.
International Search Report and Written Opinion for International Application No. PCT/IB2018/001308, dated Feb. 21, 2019.

* cited by examiner

*Primary Examiner* — Katherine M Shi
*Assistant Examiner* — Alyssa M Keane
(74) *Attorney, Agent, or Firm* — Dergosits & Noah LLP; Todd A. Noah

(57) ABSTRACT

Various embodiments are described for a stent delivery device that utilizes a push button using a slot and pin on a shuttle with a rack for slow retraction of the outer sheath as well as a flanged member connected to the outer sheath for fast retraction of the outer sheath during delivery of a self-expanding implantable device such as a stent or stent graft.

14 Claims, 9 Drawing Sheets

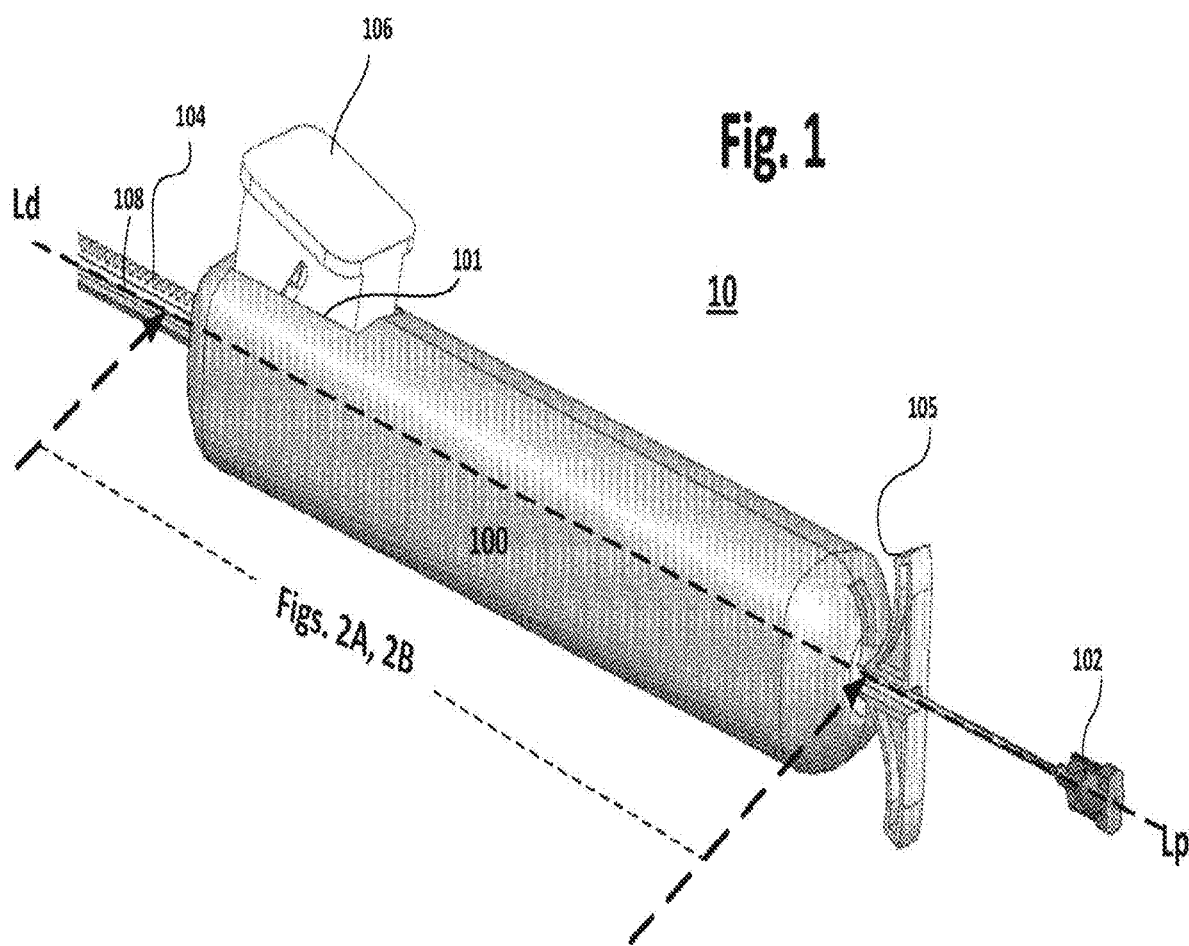

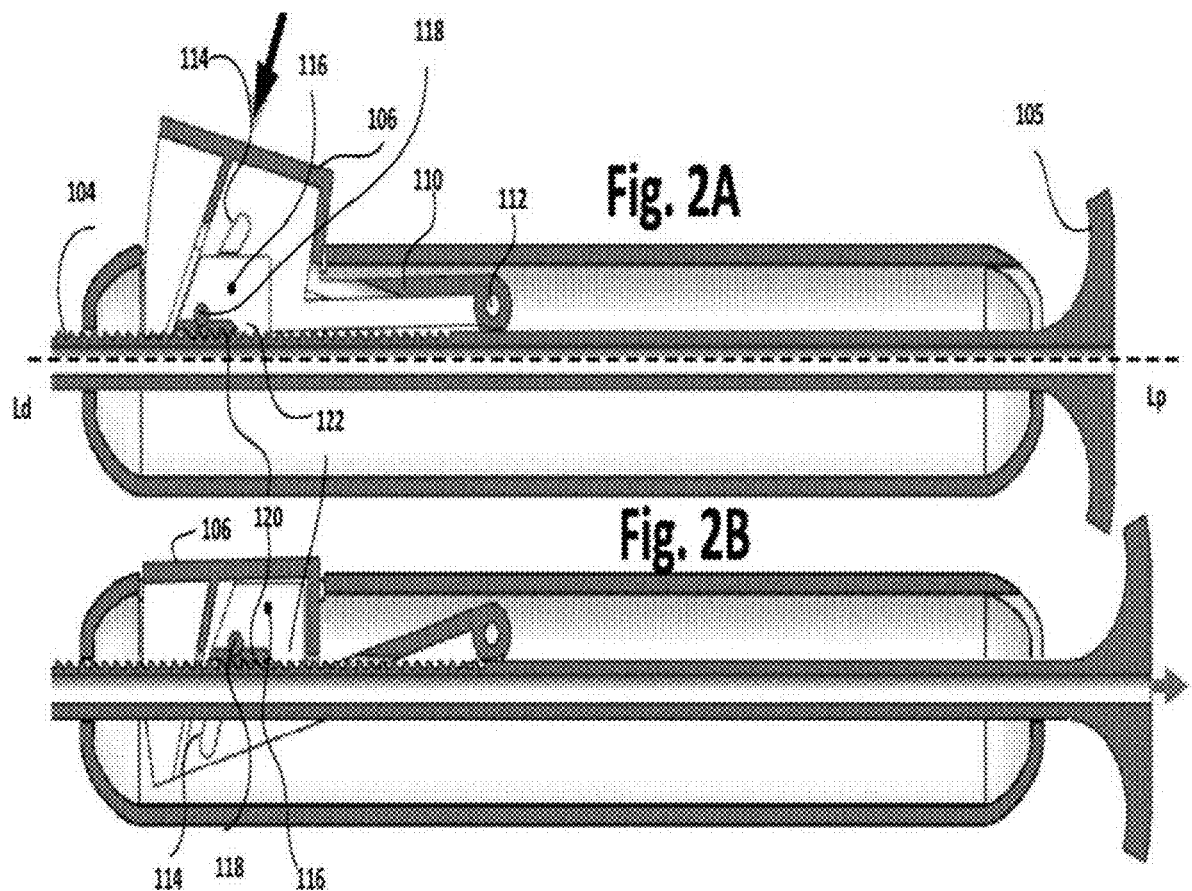
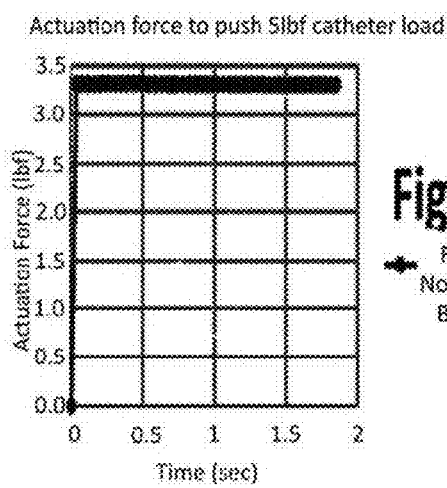
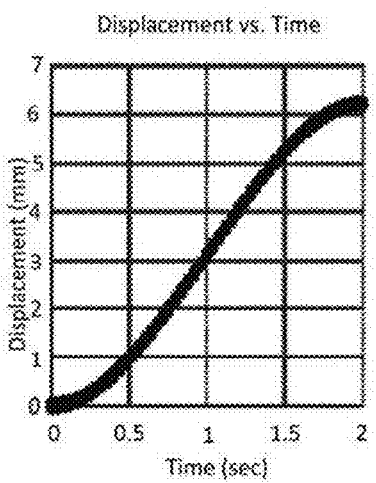

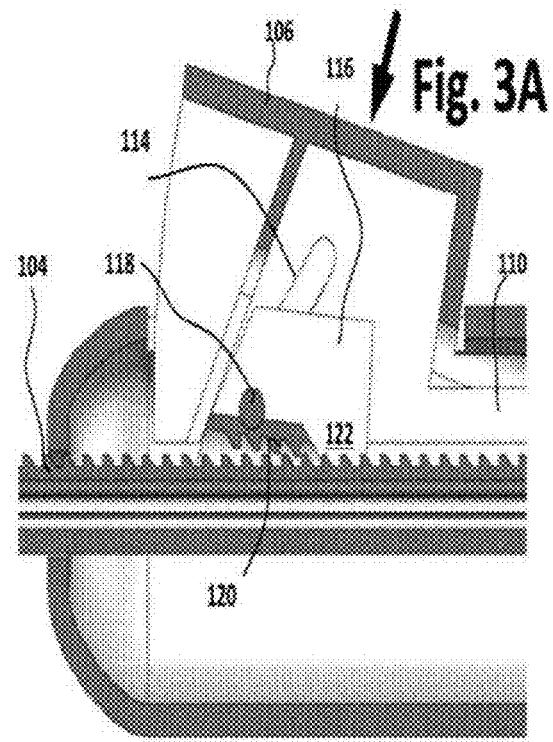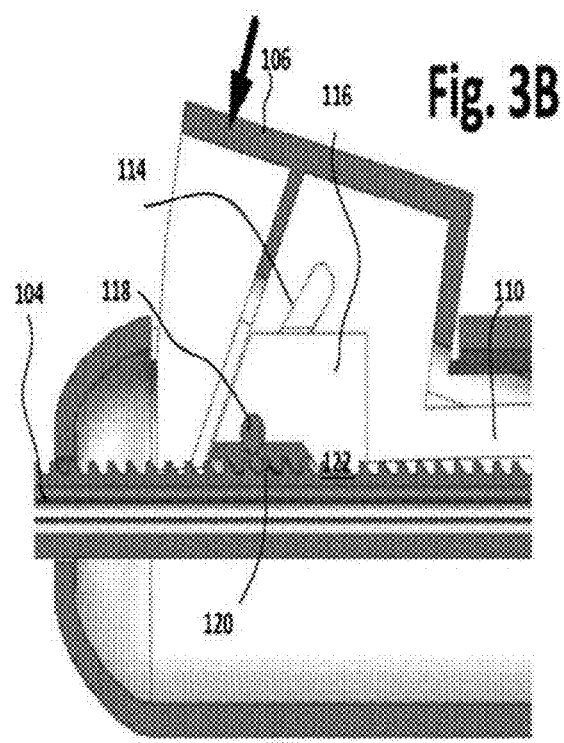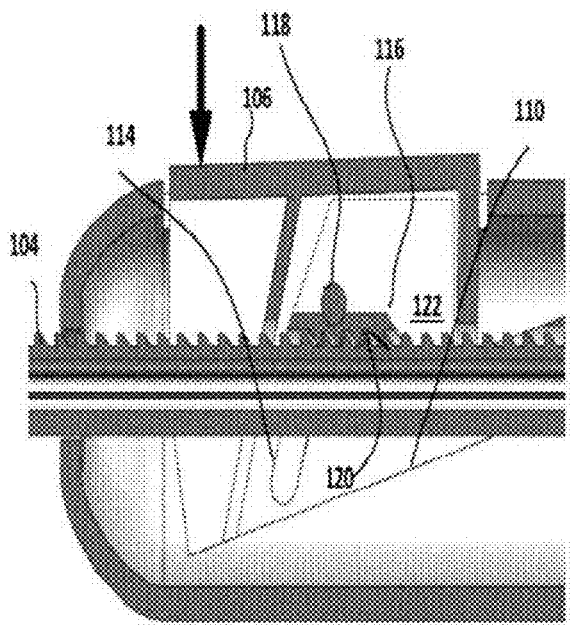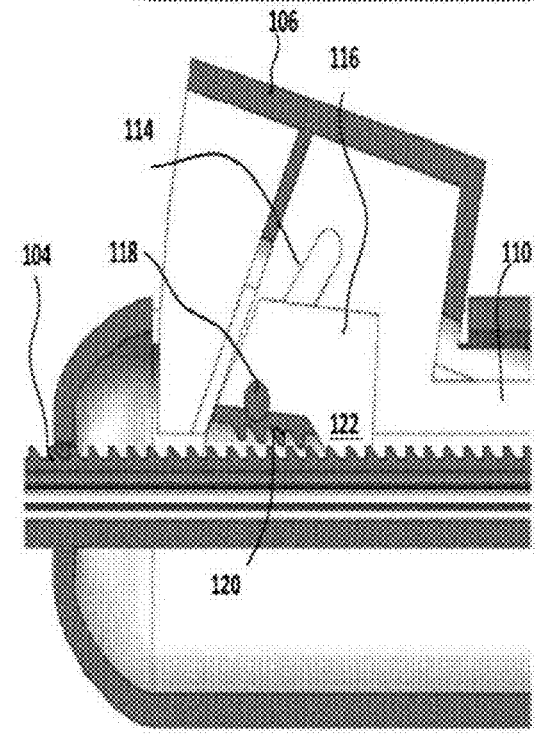

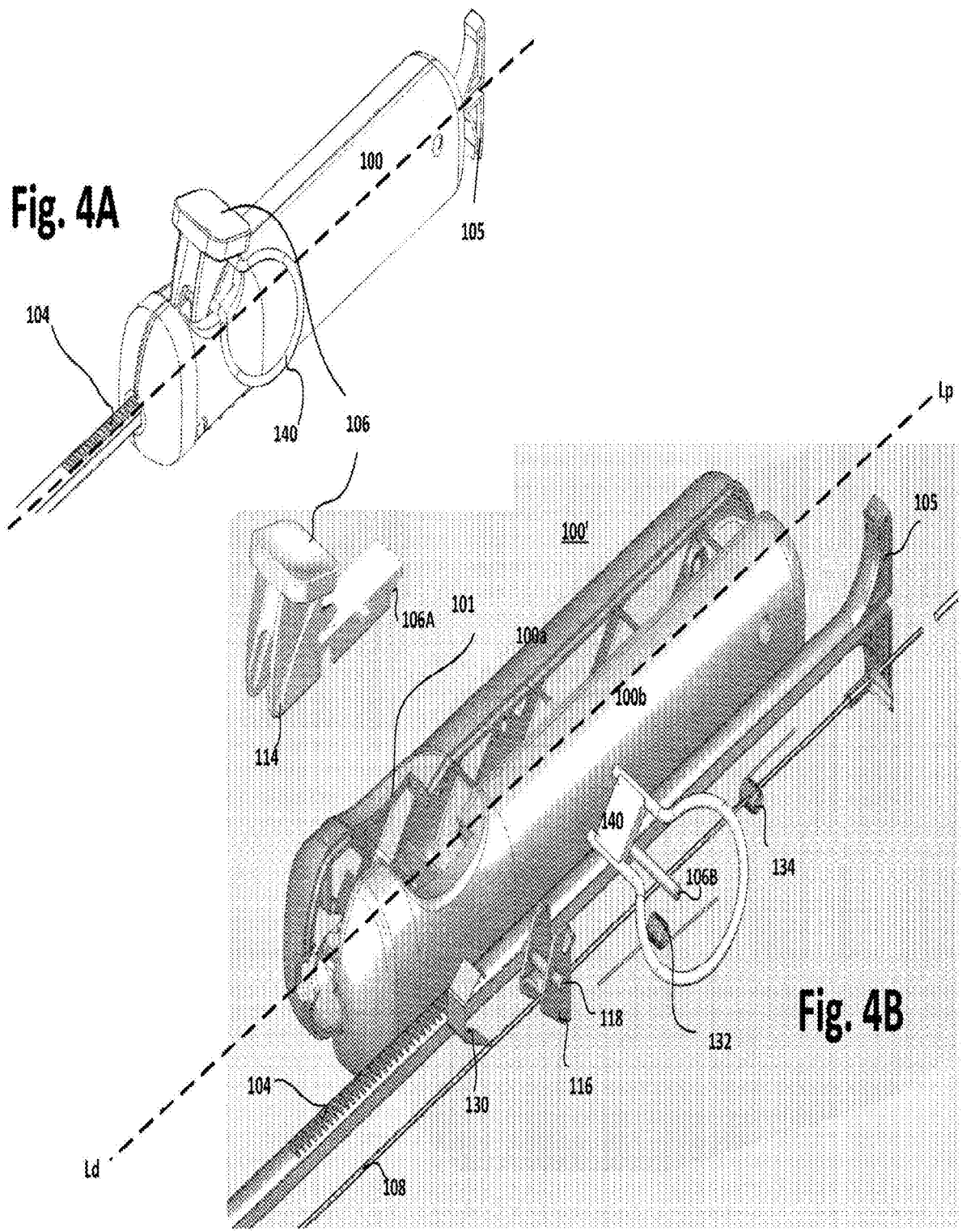

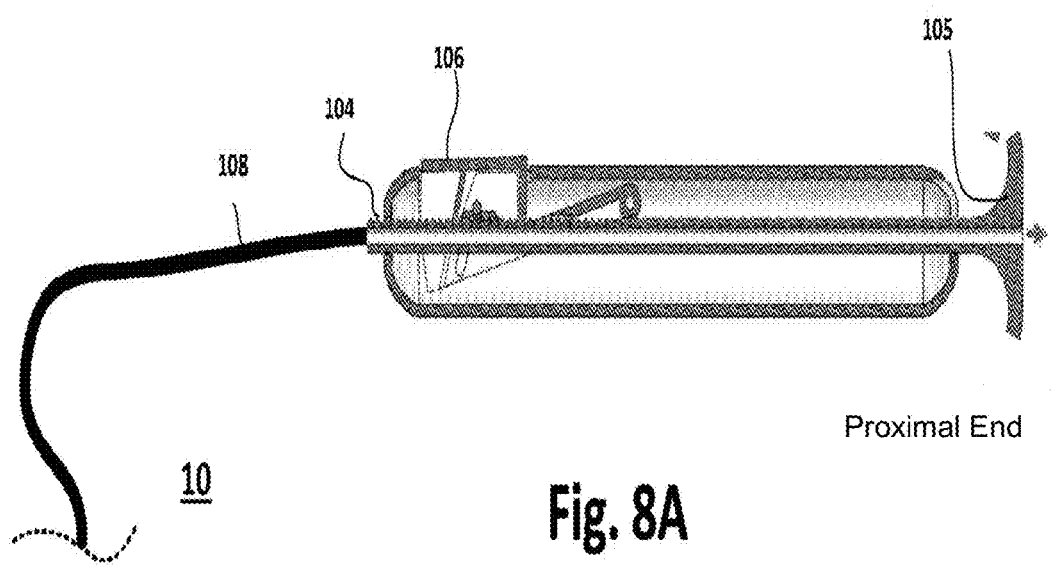
Proximal End
Fig. 8A
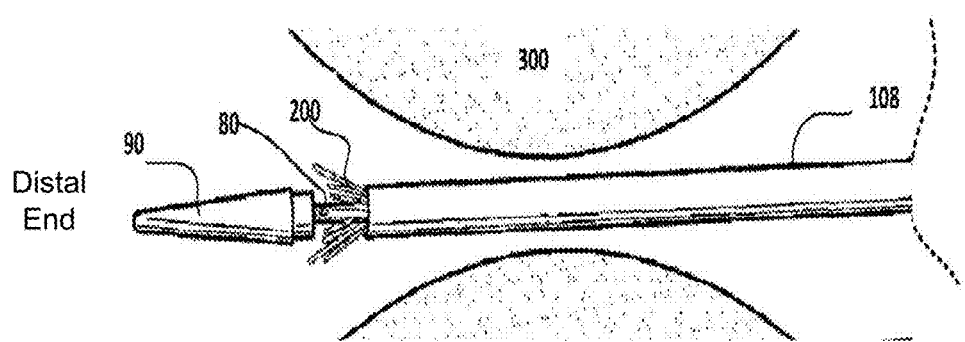
Distal End

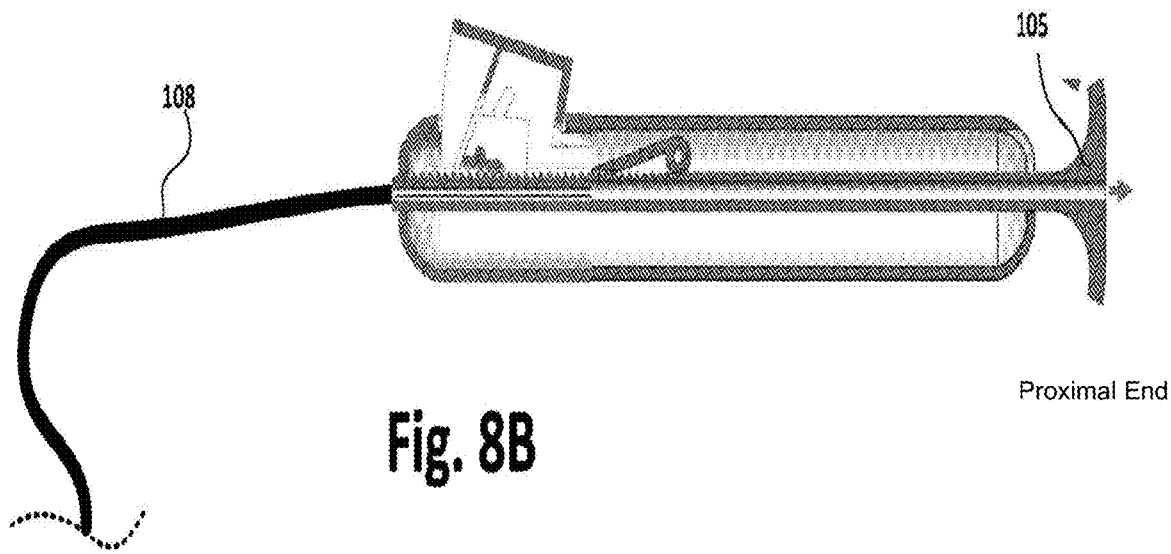
Proximal End
Fig. 8B
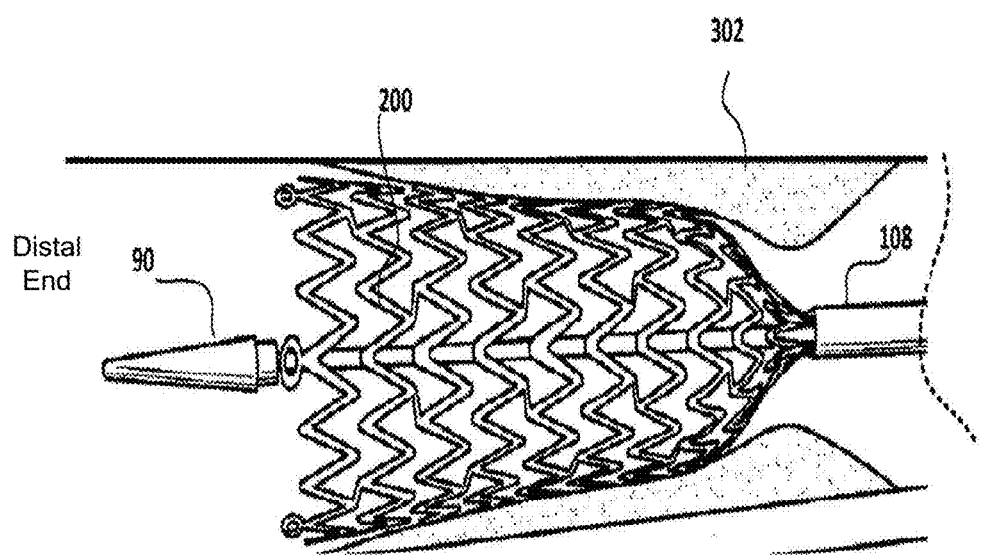

STENT DELIVERY CATHETER SYSTEM WITH SLOW SPEED CONTROL VIA PIN AND SLOT WITH FAST SPEED CONTROL TAB

PRIORITY CLAIM AND RELATED APPLICATIONS

This application claims priority under 35 U.S.C. § 119 or the Paris Convention from U.S. Provisional Patent Application 62/578,494 filed Oct. 29, 2017, the entire contents of which is incorporated herein by reference as if set forth in full herein.

BACKGROUND

It is well known to employ various intravascular endoprostheses delivered percutaneously for the treatment of diseases of various body vessels. These types of endoprosthesis are commonly referred to as "stents". A stent (which includes covered stents or stent-graft) is a generally longitudinal tubular device of biocompatible material, such as stainless steel, cobalt-chromium, nitinol or biodegradable materials, having holes or slots cut therein to define a flexible framework so they can be radially expanded, by a balloon catheter or the like, or alternately self-expanded due to its shape memory characteristic of the material within a biological vessel. The stents are usually configured as a series of hoops with each defined by cylinder-like framework. The framework is usually a series of alternating sequence of struts with a vertex between each pair of struts and configured so that the vertex of one hoop facing a vertex of the adjacent hoops may be connected together. The struts are configured to move and thereby allow the stent to be compressed or "crimped" into a smaller outer diameter so that they can be mounted inside a delivery system.

The delivery system is used to convey the stent to a desired location for treatment, and then deploy it in position. Many such stents are resiliently compressed to a smaller initial size for containment, protection, storage and eventual delivery from inside a catheter system. Upon deployment, the stents may resiliently self-expand to a larger deployed size in some embodiments or may be expanded mechanically, such as by a balloon catheter.

A successful example of a delivery catheter system, in this case for a self-expanding stent, is described in U.S. Pat. No. 6,019,778 entitled "Delivery Apparatus For A Self-Expanding Stent," to Wilson et al. issued Feb. 1, 2000. The disclosure of this patent is incorporated by reference in the present application, and generally discloses a flexible catheter system shown in a representative diagrammatic form in FIG. 10 of Wilson, including coaxially arranged inner and outer catheter members, each having a hub affixed to its proximal end. The outer sheath is described in the '778 patent as an elongated tubular member having distal and proximal ends, which is made from an outer polymeric layer, an inner polymeric layer, and a braided reinforcing layer between them. The inner shaft is described in the '778 patent as being located coaxially within the outer sheath and has a flexible tapering distal end, which generally extends distally beyond the distal end of the outer sheath. The inner shaft member also is shown as including a stop which is positioned proximal from the distal end of the outer sheath. A self-expanding stent is located within the outer sheath, and is located between the stop on the inner shaft member and the outer sheath distal end. To deploy the stent the outer sheath is withdrawn by a physician in a proximal direction, while the inner shaft member is held in position.

Additional examples of different types of known self-expanding stent delivery systems are shown in U.S. Pat. No. 4,580,568 issued to Gianturco on Apr. 8, 1986; as well as U.S. Pat. No. 4,732,152 issued to Wallsten et al., on Mar. 22, 1988.

In operation, these known stent delivery systems are generally advanced within a body of a patient along a desired vascular path or other body passageway, until the stent within the catheter system is located at a desired site for treatment. While watching the relative positions of the stent and the catheter system components with respect to a stenosis on a video x-ray fluoroscopy screen, the physician holds the proximal hub attached to the inner shaft member in a fixed position with one hand, while simultaneously gently withdrawing the proximal hub attached to the outer tubular sheath with the other hand.

For several reasons, this deployment operation may require some measure of delicate skill. For example, among these reasons is the dynamic blood flow at the desired site for treatment, which may be further disrupted by the presence of a lesion or stenosis to be treated. Another factor is the gradual resilient expansion of a stent as the outer sheath is retracted. This gradual expansion presents an opportunity for a possible reverse "watermelon-seed" phenomenon to occur. This reverse watermelon-seed phenomenon may cause the resilient stent to tend to push the outer sheath back in a proximal direction with a force that tends to change as the sheath is progressively retracted.

As a result, the physician may need to accurately hold the two proximal hubs in a specific relative position, holding them against this expansion force, while attempting to very accurately position the stent up until contact with the anatomy. One of the possibilities that may affect the positioning of the deployed stent is that the inner shaft should preferably be held stationary in the desired position. If the physician's hand that holds the inner shaft hub does inadvertently move during deployment, it is possible that the stent may be deployed in a non-optimum position.

Another possible factor is that the inner and outer catheter shaft members, like any other elongated object, do not have infinite column strength, which may present an opportunity for the position and movement of each proximal hub to differ from the position and movement of the respective distal ends of the inner and outer shaft members. Yet another factor is that the position of the stent may be adjusted up until the point at which a portion of the expanding portion of the stent touches the sidewalls of the body passage, so that the position of the stent should preferably be carefully adjusted until immediately before a portion of the stent touches the anatomy.

Some known catheter systems require two-handed operation, such as those with a pair of independent hubs, one hub on each of the inner and outer shaft members, respectively. Other known catheter systems include a pistol and trigger grip, with a single mode of deployment, involving a single trigger pull to deploy the associated stent.

SUMMARY

Applicant has devised a stent delivery system that includes a catheter tip, primary rack, and a housing. The catheter tip is coupled to an inner shaft and an outer sheath with a stent disposed between the inner shaft and the outer sheath. The inner shaft and the outer sheath extends from a distal end to a proximal end. The primary rack is connected to the outer sheath. The housing encloses a portion of the primary rack. The housing extends along a longitudinal axis from a first end to a second end. The housing includes a button and a shuttle. The button is coupled to the housing to allow for movement of the button along an arc, the button defining at least a side member generally parallel to the longitudinal axis, the side member having a slot that approximates a curve.

The shuttle is disposed partly in the button. The shuttle has a secondary rack configured to mate with a portion of the primary rack. The shuttle has a pin extending through the shuttle and the slot so that movement of the button towards the longitudinal axis forces the primary rack to translate along the longitudinal axis due to motion of the slot of the button against the pin of the shuttle.

In yet a further embodiment, applicant has devised a catheter system that includes an outer sheath, a primary rack and a housing. The outer sheath extends from a distal end to a proximal end. The primary rack is connected to the outer sheath. The housing encloses a portion of the primary rack. The housing extends along a longitudinal axis from a first end to a second end and includes a button coupled to the housing to allow for movement of the button along an arc. The button defines at least a side member generally parallel to the longitudinal axis. The side member has a slot that approximates a curve, and a shuttle disposed partly in the button. The shuttle has a secondary rack configured to mate with a portion of the primary rack with a pin extending through the shuttle and the slot so that movement of the button in a first direction toward the longitudinal axis forces the primary rack to translate along the longitudinal axis toward the second end due to motion of the slot of the button against the pin of the shuttle.

A method of delivering a self-expanding stent to selected location in a body vessel can be achieved by: moving a stent to a selected location in a body vessel, the stent being disposed adjacent a catheter tip and confined between an inner shaft and an outer sheath at a distal end of a delivery system; and applying a generally constant force over time to an actuator in a direction intersecting the longitudinal axis to translate the outer sheath at a generally constant first rate of change of distance along the longitudinal axis towards a distal end of the delivery system to allow a portion of the self-expanding stent to be expanded into the body vessel; and pulling a flange member so that the outer sheath is moved relative to the inner shaft along a direction from the distal end toward a proximal end of the delivery system at a second rate of change of distance greater than the first rate of change of distance.

For each of the embodiments described above, the following features can be utilized in various permutations with each of the embodiments. For example, the primary rack includes a flanged tab at the second end of the housing; the button is mounted to a pivot in the housing to allow for arcuate movement of the button and a tertiary rack is coupled to the shuttle to prevent movement of the primary rack along the longitudinal axis toward the first end when the tertiary rack is engaged with the primary rack. A ratchet is disposed in the housing to prevent movement of the primary rack along the longitudinal axis toward the first end; a safety pin is disposed between the button and the shuttle to prevent actuation of the button; a first biasing member is coupled to the button to bias the button in a direction opposite the first direction of the button; a second biasing member is coupled to the shuttle to bias the shuttle in the first direction of the button; the housing may include two halves that are generally symmetrical with respect to the longitudinal axis; the slot defines a spline so that a predetermined amount of force over time applied to the button results in a generally constant displacement over time of the primary rack. As well, the spline is defined by discrete points each located on respective radii of a first arc of α degrees with a radius R where each radii is separated by a second arc of β degrees and each point is located at a distance d measured from a circumference of the first arc of a degrees where $d_n = R - (X + n(0.2)(R))$ where n may be a sequence of positive integers including zero and X can be any value from 2 mm to 20 mm. For example, a may be about 12 degrees and β may be about 2 degrees and radius R may be about 60 millimeters.

These and other embodiments, features and advantages will become apparent to those skilled in the art when taken with reference to the following more detailed description of the exemplary embodiments of the invention in conjunction with the accompanying drawings that are first briefly described. As well, it is intended that these embodiments, features and advantages may be claimed in this or additional applications for patents.

BRIEF DESCRIPTION OF THE DRAWINGS

The accompanying drawings, which are incorporated herein and constitute part of this specification, illustrate presently preferred embodiments of the invention, and, together with the general description given above and the detailed description given below, serve to explain features of the invention (wherein like numerals represent like elements), in which:

FIG. 1 illustrates a perspective view of a handle according to an embodiment;

FIGS. 2A and 2B illustrate sectioned side views of an embodiment of the handle in FIG. 1 during an initial state and a final state;

FIGS. 2C and 2D illustrate respectively the input force over time and resulting distance traveled over time typical of a handle according to FIG. 1;

FIGS. 3A, 3B, 3C, and 3D illustrate close-up view of the operation of the handle in FIG. 1;

FIGS. 4A and 4B illustrate yet another embodiment of the handle in FIG. 1 with the principles of FIGS. 1-3;

FIGS. 8A and 8B illustrate the operation of the system, according to an embodiment.

DETAILED DESCRIPTION

Figure 5:
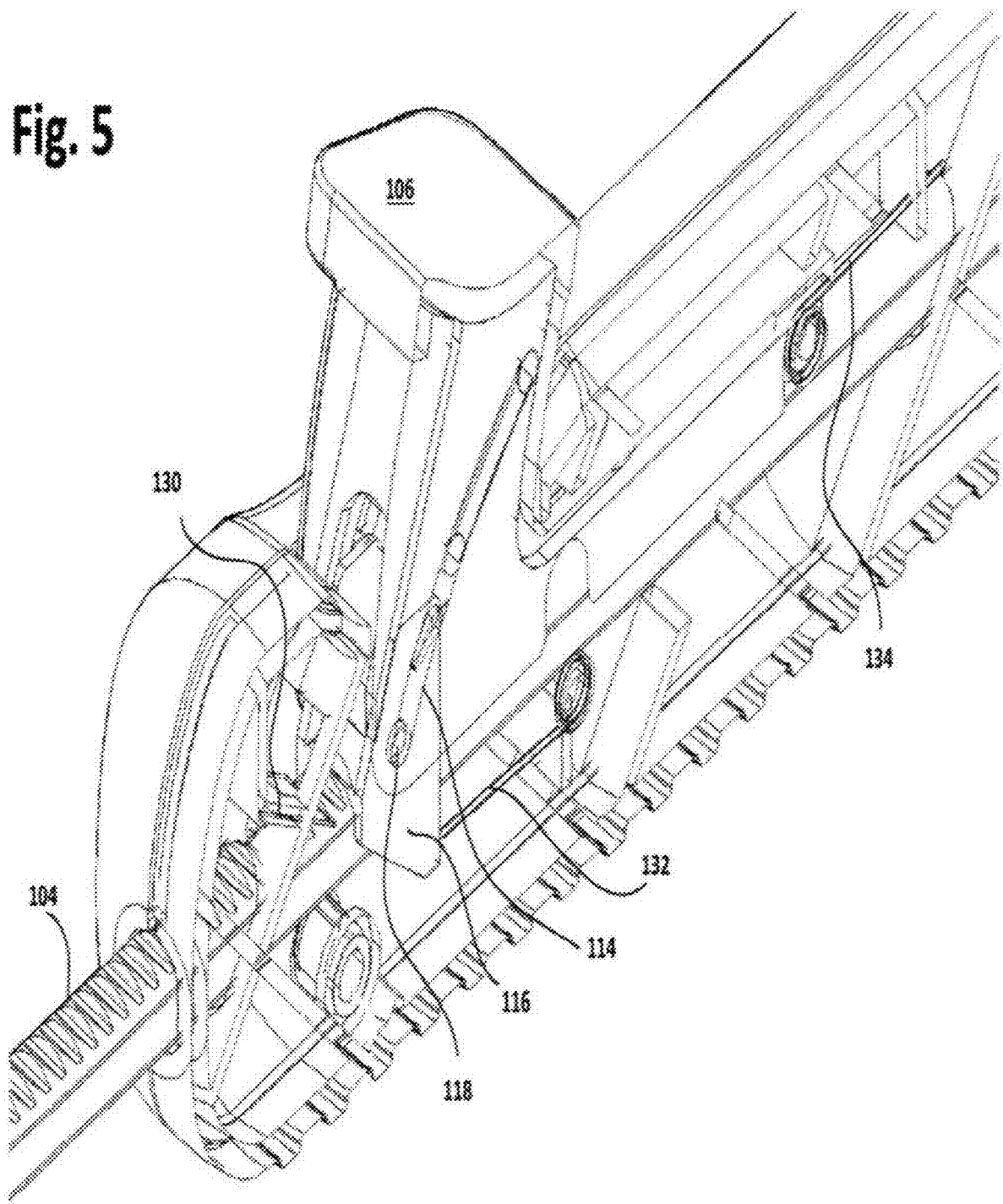
FIG. 5 illustrates a close-up perspective of the handle with the principles of FIGS. 1-3.

The following detailed description should be read with reference to the drawings, in which like elements in different drawings are identically numbered. The drawings, which are not necessarily to scale, depict selected embodiments and are not intended to limit the scope of the invention. The detailed description illustrates by way of example, not by way of limitation, the principles of the invention. This description will clearly enable one skilled in the art to make and use the invention, and describes several embodiments, adaptations, variations, alternatives and uses of the invention, including what is presently believed to be the best mode of carrying out the invention.

As used herein, the terms "about" or "approximately" for any numerical values or ranges indicate a suitable dimensional tolerance that allows the part or collection of components to function for its intended purpose as described herein. More specifically, "about" or "approximately" may refer to the range of values ±10% of the recited value, e.g. "about 90%" may refer to the range of values from 81% to 99%. In addition, as used herein, the terms "patient," "host," "user," and "subject" refer to any human or animal subject and are not intended to limit the systems or methods to human use, although use of the subject invention in a human patient represents a preferred embodiment. The term "stent" is intended to encompass an uncovered framework as well as one that is covered by a suitable material (e.g., stent-graft). The term "proximal" is used to denote the location closer to the operator and "distal" is used to denote a location further away from the operator or the health care provider.

Referring now to the figures wherein like numerals indicate the same element throughout the views, there is shown in FIG. 1 a portion of the delivery system 10 in the form of a handle that defines a housing 100. The housing 100 extends along a longitudinal axis Ld-Lp from a proximal end to a distal end. The housing 100 provides a slot 101 that extends along a portion of the longitudinal axis Ld-Lp. An outer sheath 108 is configured for movement along the longitudinal axis Ld-Lp by being coupled to a slider rack 104 disposed in and through housing 100. The slider rack 104 is attached to a flanged slider tab 105 so that the entire rack 104 can be pulled toward the proximal end very quickly. A luer fitting 102 is provided at the proximal end Lp. A push button 106 can be actuated by a finger, preferably a thumb of the operator to allow for slow retraction of the sheath 108 during deployment of the stent.

FIG. 2A illustrates the internal mechanism of the handle 100 in a sectioned plan view. In particular, FIG. 2A illustrates the position of push button 106 in an initial state of the handle 100 while FIG. 2B illustrates the position of the button 106 in relation to the slider rack 104 when the button 106 is fully actuated or depressed.

Referring to FIG. 3A, forces (arrow) can be applied to the button 106 so that the button 106 moves in a downward direction (arrow) relative to the axis Ld-Lp. Button 106 is mounted to a pivot point 112 (shown in FIG. 1) to allow for arcuate movement of button 106 in a direction towards the longitudinal axis (or even intersecting the longitudinal axis Ld-Lp). A shuttle 116 is disposed partly inside button housing 106. Mounted to shuttle 116 is pin 118. Button 106 is provided with a slot 114 in which pin 118 is mounted for movement, such as in a side member of button 106 that may be relatively parallel with axis Ld-Lp. As force is applied to button 106 to move it toward the longitudinal axis in FIG. 3B, pin 118 is constrained in its motion by slot 114 to translate linearly along the longitudinal axis. As pin 118 is connected to the secondary rack 120, secondary rack 120 must move, shown here in FIG. 3C. Movement of secondary rack 120 forces the primary rack 104 to also move due to the coupling of the teeth (or pawls) between the primary rack 104 and secondary rack 120. Of note is that the embodiments described herein allow for a generally constant force applied over time (i.e., constant force rate of change in FIG. 2C) to provide a generally constant distance traveled over time (i.e., rate of change of distance in FIG. 2D). Once force is released, biasing members (shown elsewhere) allow the button to return to its initial state as well as allowing a tertiary rack 122, as part of shuttle 116, to engage against the primary rack 104 to prevent a movement of primary rack 104 toward the distal end. Ratchet (shown elsewhere) can also be utilized in place of or in addition to tertiary rack 122 to prevent this reversed movement of the outer sheath 108 toward the distal end.

Figure 6:
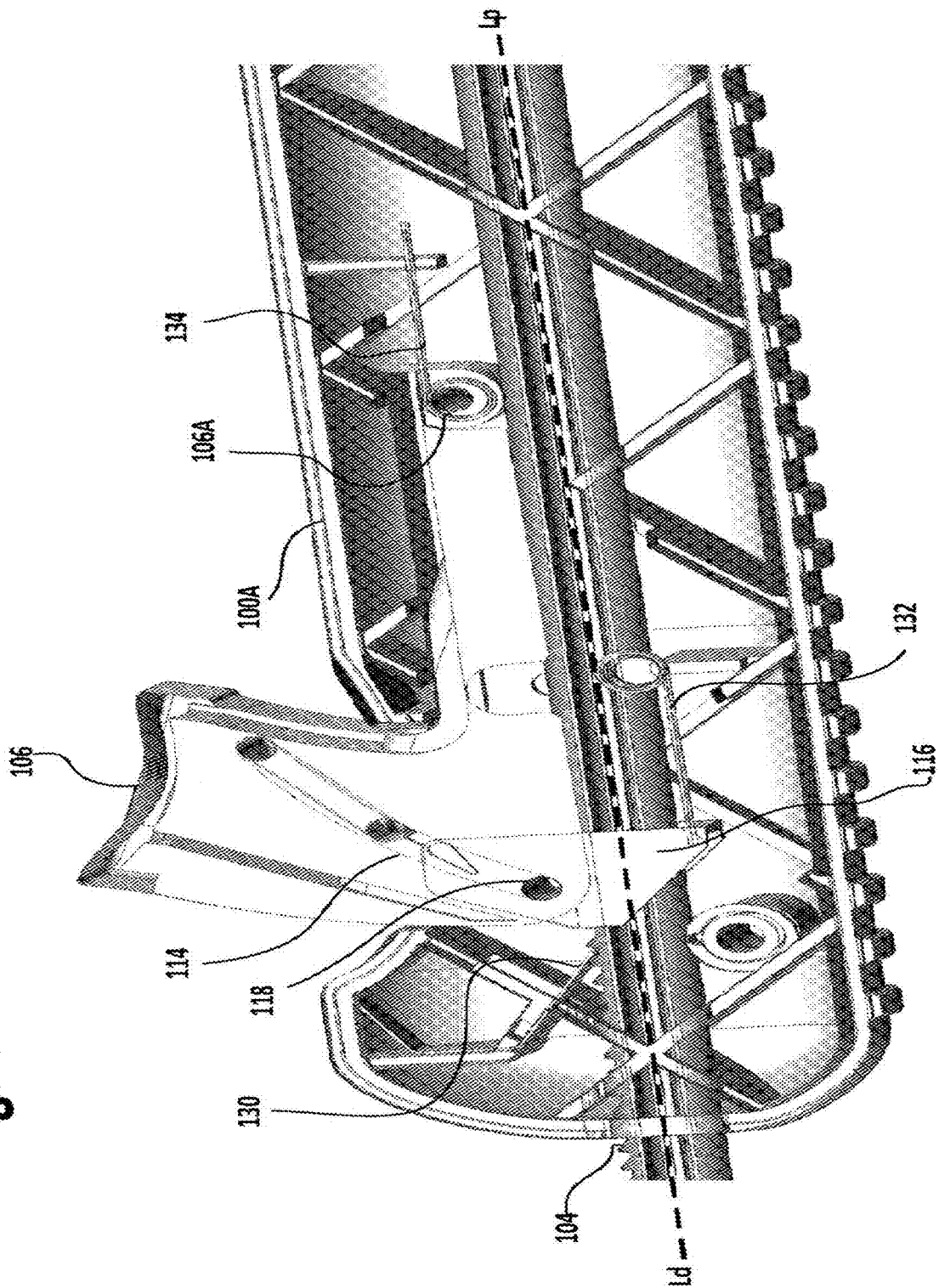
FIG. 6 illustrates a close-up plan view of a section of the embodiment of FIG. 3.

FIGS. 4A and 4B illustrate yet another variation 100' of the catheter handle device usable in the delivery system 10. In particular, FIG. 4A illustrates the complete handle with safety lock 140 in a more ergonomic design. In addition to the common components illustrated earlier (referenced with the same reference numerals) the exploded view of FIG. 4B shows a two-part housing (100a and 100b) that houses the button 106 connected to the housing 100' via pivot opening 106A in which a pin 106B can be inserted and supported via housings 100a and 100b. As shown also in FIGS. 5 and 6, a ratchet 130 is provided to prevent primary rack 104 from moving distally. Torsion spring 132 is disposed in the housing to bias the shuttle 116 toward engagement with rack 104. Torsion spring 104 is disposed in the housing to bias actuator 106 towards its initial position. As in the embodiment 100, slot 114 can be configured in any shape such as, for example, linear, curvilinear or arcuate. In the embodiments illustrated and described here, applicant has devised the system 10 to achieve constant rate of change of distance in the retraction of the sheath for constant rate of force applied to actuator 106. To achieve this, a spline S (FIG. 7) was derived.

Figure 7:
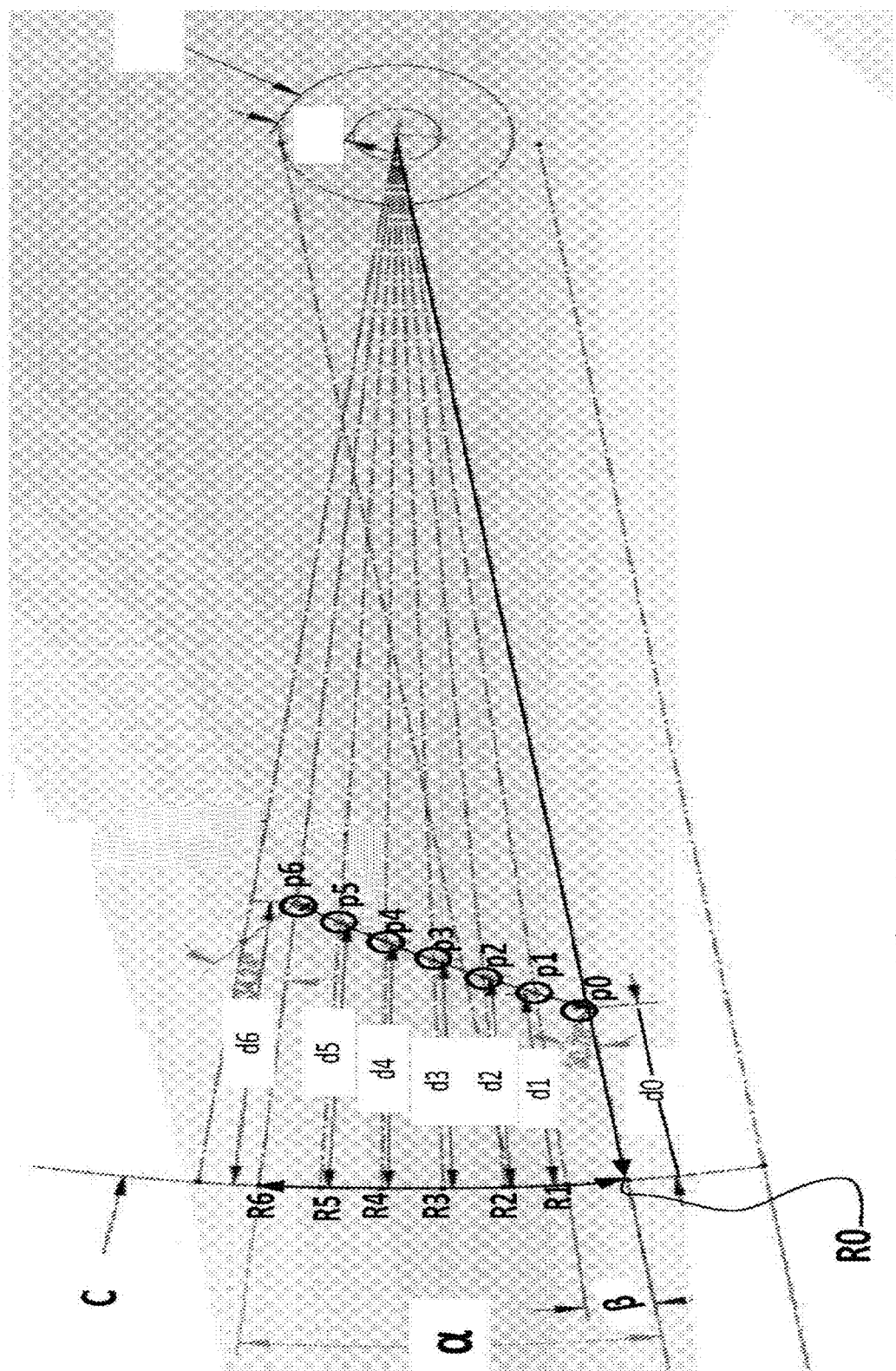
FIG. 7 illustrates a spline that define the path of the pin in the embodiments described and illustrated herein.

As shown in FIG. 7, the spline S in which a path (i.e., slot 114) of pin 118 must follow is defined by discrete points (p0, p1, p2, p3 . . . p6) each located on respective radii (R0, R1, R2, . . . R6) of a first arc C of α degrees with a radius R where each radii is separated by a second arc of β degrees and each point is located at a distance $d_n$ measured from a circumference of the first arc C of α degrees where $d_n = R - (X + n*(0.2)*(R))$ where n comprises a sequence of positive integers including zero and X can be any value from 2 mm to 20 mm, while a can be from 5 to 45 degrees and β can be from 1 to 10 degrees. In the example described and illustrated here, R is about 60 mm, X is about 10 mm; d0 is about 10 mm; d1 is about 11.05 mm; d2 is about 12.1 mm; d3 is about 13.2 mm; d4 is about 14.2 mm; d5 is about 15.3 mm and d6 is about 16.3 mm while a is about 12 degrees and β is about 2 degrees. It should be noted that this is but one example and that many other examples can be derived using the empirical technique and range for variables R, X, n, α and β as devised by applicant.

In operation as schematically indicated in FIGS. 8A and 8B, the distal end of the medical device delivery system 10 is preferably directed into a patient via a body passageway 300. The medical device delivery system 10 may preferably follow along a guidewire (not shown) or travel through a previously placed guiding catheter (not shown), until the distal tip 90 is at a desired location in the body vessel 300 for treatment. As shown in FIG. 8B, the distal tip 90 has preferably crossed the site of a lesion or stenosis 302. When the device is properly in an initial position (FIG. 8A), the physician releases or removes the safety lock 140 of the handle (not shown for brevity). The lock may be releasable only once, or may be capable of repeatedly being engaged and released. Such a locking mechanism preferably resists inadvertent or accidental movement or retraction of the stent delivery system components during packaging, sterilization, shipping, storage, handling and preparation.

After the lock is released, the actuator 106 can be depressed such that the outer sheath 108 is retracted towards the operator. The use of the actuator 106 coupled to the outer sheath 108 allows precise and sensitive adjustment to pull the outer sheath 108 back slightly. This small movement exposes a small portion of the medical device, in this case a stent 200, as shown in FIG. 8A. In this configuration, the handle 100 will hold the outer sheath 108 in position relative to the inner wire SO, resisting further inadvertent expansion of the stent 200. The physician then has the time and flexibility of procedure to selectively optimize and make any final adjustments to the position of the medical device and delivery system within the desired site, as illustrated in FIG. 8A This precise adjustment of the position of the stent 200, before any portion of the stent 200 touches the body passage or vessel 300 in a manner that might inhibit further positional adjustment, is preferable.

When the physician is satisfied with the positioning, as it appears on a fluoroscopic x-ray video screen, the physician may continue to rotate the actuator 106 to further withdraw the outer sheath 108, as shown in FIG. 8B.

Upon initial contact of the stent 200 with the vessel wall, or when the stent is 200 expanded sufficiently to independently hold its position, or at any desired point, the physician may simply grasp flange 105 to pull slider rack 104 in the distal direction. This second mode of withdrawing the outer sheath 108 allows relatively large-scale and rapid movement, at whatever speed the physician wishes, to quickly deploy the medical device.

Various materials may be selected for the components of the present invention, including any material having the desirable performance characteristics. In the particular embodiment shown in the drawings, the inner and outer shaft members and, strain relief and distal tip may be made of any biocompatible and suitably flexible yet sufficiently strong material, including polymers of various types. Possible selections for such materials include nylons or polyamides, polyimides, polyethylenes, polyurethanes, polyethers, polyesters, etc. In the alternative, some portion or all of the inner and/or outer shaft member may be formed of a flexible metal, including for example stainless steel or nitinol hypotube. The stent 200 is preferably made of any biocompatible material that is strong and rigid, including for example stainless steel, platinum, tungsten, etc. The components of the handle of the present invention are preferably made of a material that is strong and rigid, including for example inflexible polycarbonates, or even some metal components. In addition, the inner shaft member distal tip may preferably be provided with a through lumen adapted to receive a guidewire.

Of course, many different variations are included within the scope of the present invention. Some of these variations or alternative embodiments include any possible arrangement of sizes, materials, and designs within the scope of the claims.

By virtue of the disclosure provided herein, a method of moving a stent to a selected location in a body vessel is provided. The stent is disposed adjacent a catheter tip and confined between an inner shaft and an outer sheath at a distal end of a delivery system The method includes applying a generally constant force over time to an actuator in a direction intersecting the longitudinal axis to translate the outer sheath at a generally constant first rate of change of distance along the longitudinal axis towards a distal end of the delivery system to allow a portion of the self-expanding stent to be expanded into the body vessel; and subsequently pulling a flange member after desired positioning of the stent so that the outer sheath is moved relative to the inner shaft along a direction from the distal end toward a proximal end of the delivery system at a second rate of change of distance greater than the first rate of change of distance.

While the invention has been described in terms of particular variations and illustrative figures, those of ordinary skill in the art will recognize that the invention is not limited to the variations or figures described. In addition, where methods and steps described above indicate certain events occurring in certain order, it is intended that certain steps do not have to be performed in the order described but in any order as long as the steps allow the embodiments to function for their intended purposes. Therefore, to the extent there are variations of the invention, which are within the spirit of the disclosure or equivalent to the inventions found in the claims, it is the intent that this patent will cover those variations as well.

What is claimed is:

1. A stent delivery system comprising
a catheter tip coupled to an inner shaft and an outer sheath with a stent disposed between the inner shaft and the outer sheath, the inner shaft and the outer sheath extending from a distal end to a proximal end;
a primary rack connected to the outer sheath; and
a housing enclosing a portion of the primary rack, the housing extending along a longitudinal axis from a first end to a second end, wherein the housing includes:
a button coupled to the housing to allow for movement of the button along an arc, the button defining at least a side member generally parallel to the longitudinal axis, the side member having a slot that approximates a curve; and
a shuttle disposed partly in the button, the shuttle having a secondary rack configured to mate with a portion of the primary rack, the shuttle having a pin extending through the shuttle and the slot so that movement of the button towards the longitudinal axis forces the primary rack to translate along the longitudinal axis due to motion of the slot of the button against the pin of the shuttle.

2. A catheter system comprising:
an outer sheath extending from a distal end to a proximal end;
a primary rack connected to the outer sheath; and
a housing enclosing a portion of the primary rack, the housing extending along a longitudinal axis from a first end to a second end, the housing includes:
a button coupled to the housing to allow for movement of the button along an arc, the button defining at least a side member generally parallel to the longitudinal axis, the side member having a slot that approximates a curve; and
a shuttle disposed partly in the button, the shuttle having a secondary rack configured to mate with a portion of the primary rack, the shuttle having a pin extending through the shuttle and the slot so that movement of the button in a first direction toward the longitudinal axis forces the primary rack to translate along the longitudinal axis toward the second end due to motion of the slot of the button against the pin of the shuttle.

3. The system of claim 1 or claim 2, wherein the primary rack includes a flanged tab at the second end of the housing.

4. The system of claim 1 or claim 2, wherein the button is mounted to a pivot in the housing to allow for arcuate movement of the button.

5. The system of claim 1 or claim 2, wherein a tertiary rack is coupled to the shuttle to prevent movement of the primary rack along the longitudinal axis toward the first end when the tertiary rack is engaged with the primary rack.

6. The system of claim 1 or claim 2, wherein a ratchet is disposed in the housing to prevent movement of the primary rack along the longitudinal axis toward the first end.

7. The system of claim 1 or claim 2, wherein a safety pin is disposed between the button and the shuttle to prevent actuation of the button.

8. The system of claim 1 or claim 2, wherein a first biasing member is coupled to the button to bias the button in a direction opposite the first direction of the button.

9. The system of claim 1 or claim 2, wherein a second biasing member is coupled to the shuttle to bias the shuttle in the first direction of the button.

10. The system of claim 1 or claim 2, wherein the housing comprises two halves that are generally symmetrical with respect to the longitudinal axis.

11. The system of claim 1 or claim 2, wherein the slot defines a spline so that a predetermined amount of force over time applied to the button results in a generally constant displacement over time of the primary rack.

12. The system of claim 11, wherein the spline is defined by discrete points each located on respective radii of a first arc of a degrees with a radius R where each radii is separated by a second arc of β degrees and each point is located at a distance d measured from a circumference of the first arc of a degrees where $d_n = R - (X + n(0.2)(R))$ where n comprises a sequence of positive integers including zero and X can be any value from 2 mm to 20 mm.

13. The system of claim 12, wherein a comprises about 12 degrees and β comprises about 2 degrees.

14. The system of claim 13, wherein radius R comprises about 60 millimeters.

\* \* \* \* \*